United States Patent [19]

Kossiakoff et al.

[11] Patent Number: 4,995,407
[45] Date of Patent: Feb. 26, 1991

[54] NON-COMBUSTIBLE ARTIFICIAL CIGARETTE

[75] Inventors: Nicolas Kossiakoff, Chambourcy; Daniel Augis, Nanterre, both of France

[73] Assignee: International Flavors & Fragrances, Inc., New York, N.Y.

[21] Appl. No.: 384,727

[22] Filed: Jul. 25, 1989

[51] Int. Cl.$^5$ .................. A24D 3/00; A24F 47/00
[52] U.S. Cl. .................. 131/359; 131/273; 131/369
[58] Field of Search ............. 131/270, 273, 359, 369

[56] References Cited

U.S. PATENT DOCUMENTS

| Re. 4,962 | 7/1872 | Wright | 131/275 |
| 937,801 | 10/1909 | Heddles | 131/275 |
| 2,445,476 | 7/1948 | Folkman | 131/273 |
| 4,670,264 | 6/1987 | Warren et al. | |

FOREIGN PATENT DOCUMENTS 3637319  5/1988  Fed. Rep. of Germany

Primary Examiner—V. Millin
Attorney, Agent, or Firm—Brooks Haidt Haffner & Delahunty

[57] ABSTRACT

An artificial cigarette is constructed with a paper stock tube plugged at both ends by a porous body and containing a quantity of beads or pellets of a vapor emitting composition where the composition includes at least one or more stress reactivity-reducing substances selected from the group consisting of nutmeg oil, mace extract, neroli oil, valerian oil, myristicin, elemicin, and isoelemicin. The contents of the tube can be augmented by filler materials and one or more substances selected from the group consisting of flavoring materials and aromatic materials.

17 Claims, 3 Drawing Sheets

NON-COMBUSTIBLE ARTIFICIAL CIGARETTE

BACKGROUND OF THE INVENTION

The present invention relates to an artificial cigarette. In particular, it relates to an article containing no tobacco and no nicotine and which is smokeless.

The difficulty in providing an acceptable artificial cigarette is in trying to give the consumer the flavor and feel of a real cigarette along with a physiological impact as satisfying as that derived from the nicotine in tobacco.

In Warren et al. patent No. 4,670,264, issued June 2, 1987 to International Flavors & Fragrances as assignee of the inventors, there is described a method for reducing physiological and/or subjective reactivity to stress in humans being subjected to stress conditions. The method consists of administering to such humans an effective amount of a physiological and/or subjective stress reactivity-reducing substance selected from the group consisting of: (i) nutmeg oil; (ii) mace extract; (iii) neroli oil; (iv) valerian oil; (v) myristicin; (vi) isoelemicin; and (vii) elemicin. Administration is through inhalation or transdermally using one or more of the above ingredients alone or in a suitable composition such as an ethanol and/or a perfume composition, a cologne or perfumed article (e.g., air freshener or deodorant stick.) For a complete discussion of the effect of the above substances on stress in humans, reference should be had to said Warren et al. patent which is incorporated herein by reference.

The Warren et al. patent discloses a preferred method for preparing compositions for use as taught therein. A thermoplastic polymer, e.g., polyethylene, is heated until liquified whereupon the active ingredients are added, blended with the polymer, then discharged through a series of orifices onto a cold substrate, a moving conveyer, thereby producing a quantity of beads or pellets capable of emitting stress relieving vapors when incorporated in a deodorant stick or deodorant soap or other perfumed article.

SUMMARY OF THE PRESENT INVENTION

With the foregoing as background, it is an object of the present invention to provide an artificial cigarette.

It is a further object to provide such artificial product with the ability to generate user acceptance as a cigarette-like article without containing a nicotinic substance.

A still further object is to provide an artificial cigarette having an impact on stress induced stress thereby providing the user with a sense of heightened well being.

Other objects will appear to those skilled in the subject art after reading the detailed description to follow of the presently preferred embodiments of the invention.

In accordance with one aspect of the present invention there is provided a non-combustible artificial cigarette comprising a tube resembling a cigarette that is closed at both ends by porous plugs and which confines a quantity of a vapor emitting material where said material includes at least one or more stress reactivity-reducing substances selected from the group consisting of nutmeg oil, mace extract, neroli oil, valerian oil, myristicin, elemicin, and isoelemicin, and optionally one or more substances selected from the group consisting of flavoring materials and aromatic materials. The quantity of the vapor emitting material is chosen sufficient to evolve, during the act of oral inhalation through said tube, a physiologically effective amount of vapor which becomes entrained in the inhalant. By "physiologically effective" is meant that it is sufficient to provide the user with a sense of satisfaction.

BRIEF DESCRIPTION OF THE DRAWINGS

The invention will be understood better after reading the following detailed description of the presently preferred embodiments thereof with reference to the appended drawings in which.

The same reference numerals are used to describe the same or similar components throughout the Figures of the drawings.

DETAILED DESCRIPTION OF THE PRESENTLY PREFERRED EMBODIMENTS

Figure 8:
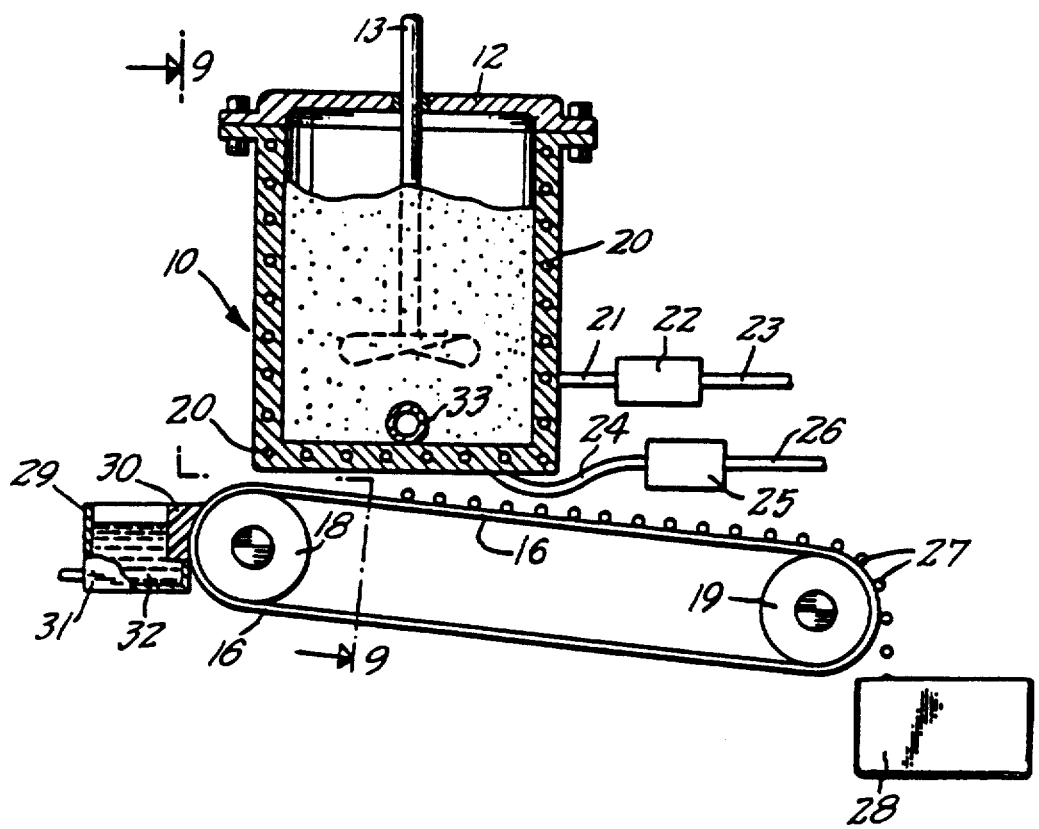
FIG. 8 is a cutaway side elevational view of apparatus used in preparing the stress reactivity-reducing substance-containing beads of the invention.
Figure 9:
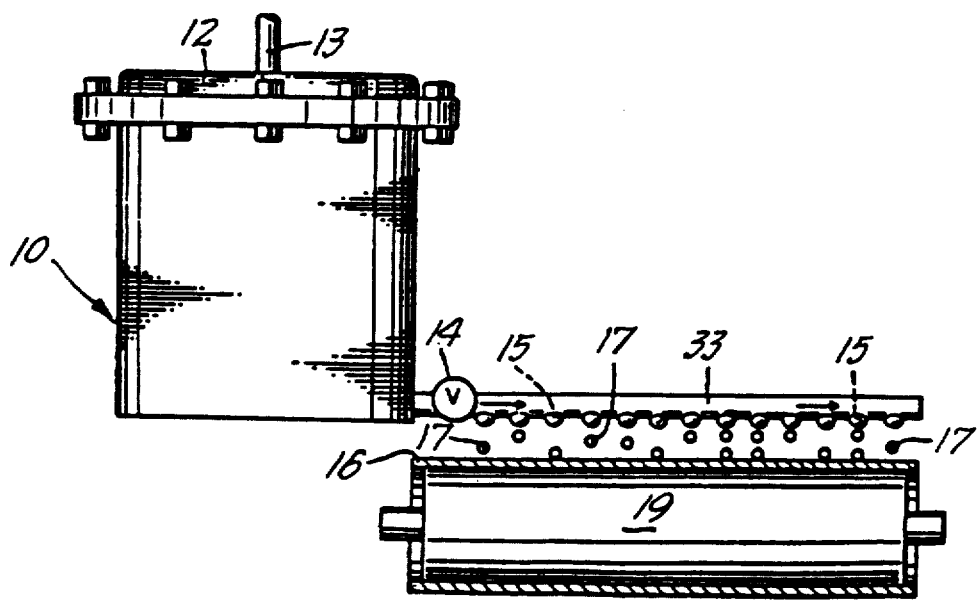
FIG. 9 is a cross-sectional view taken along line 6—6 of FIG. 8.

Referring initially to FIGS. 8 and 9, there is illustrated therein a preferred method for preparing compositions for the practice of the present invention. A thermoplastic polymer, e.g., polyethylene, is heated to about 220°–250° F. in a container 10 of the kind illustrated in FIGS. 8 and 9. A formulation containing one or more stress reactivity-reducing substances enumerated above, and optionally one or more substances selected from the group consisting of flavoring materials and aromatic materials, is then quickly added to the liquified thermoplastic polymer. The lid 12 is put in place and the agitating means 13 is actuated. The temperature is maintained at about 225° F. and the mixing is continued for about 5 to 15 minutes. The valve 14 (see FIG. 9) in pipe 33 is then opened to allow flow of the molten thermoplastic polymer enriched with the stress reactivity-reducing substances and flavoring or aromatic materials, if present, to exit through the orifices 15. The liquid falling through the orifices 15 solidifies almost instantaneously on impact with moving cooled conveyor 16. The thermoplastic polymer beads or pellets 17 having pronounced physiological and/or subjective reactivity reduction effects (to stress) are thus formed.

The conveyor 16 is moved using conveyor rollers 18 and 19. The vessel 10 is heated using heating coils 20 powered by power supplies indicated by reference numerals 21, 22, 23, 24, 25 and 26. The solidified beads containing stress reactivity reduction "active(s)", indicated by the numeral 27, travel into container 28 where they are held for subsequent processing. The conveyor is cooled using a cooling device indicated by reference numerals 29, 30, 31 and 32.

Figure 1:
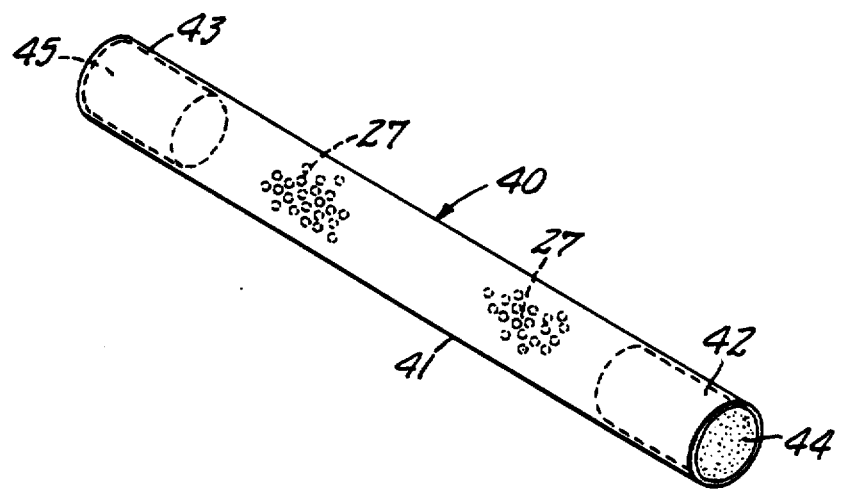
FIG. 1 is a perspective view of an artificial cigarette constructed in accordance with the present invention.
Figure 2:
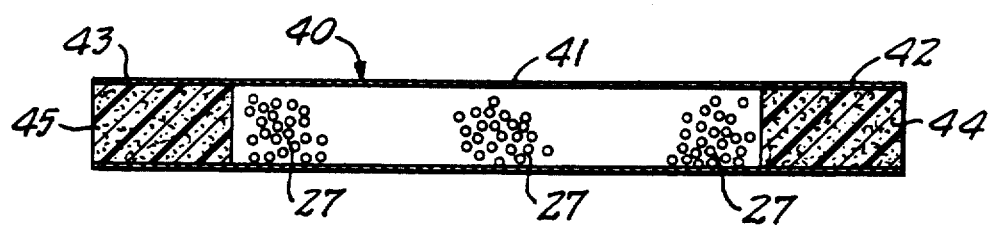
FIG. 2 is a longitudinal sectional view through the cigarette of FIG. 1.

Now, referring to FIGS. 1 and 2, there is shown, designated generally by the reference numeral 40, a non-combustible artificial cigarette embodying the present invention. The cigarette 40 comprises a tube 41 of paper stock or the like resembling a tobacco filled cigarette in both appearance and tactile sensation. The tube 41 is closed at both ends, 42 and 43, by porous plugs 44 and 45, respectively. As used herein, the term "porous" is intended to mean vapor permeable. However, the material from which the plugs are fabricated should be hydrophobic.

Between the plugs 44 and 45, within the tube 41, is confined a quantity of vapor emitting material, e.g., in the form of the beads 27 produced as previously described. The vapor emitting material includes at least one or more stress reactivity-reducing substances selected from the group consisting of nutmeg oil, mace extract, neroli oil, valerian oil, myristicin, elemicin, and isoelemicin. In addition, the vapor emitting material may include one or more substances selected from the group consisting of:(a) flavoring materials such as: saturated, unsaturated, fatty and amino acids; alcohols, including primary and secondary alcohols; esters, carbonyl compounds, including ketones and aldehydes; lactones; cyclic organic materials including benzene derivatives, alicyclics, hetero-cyclics such as furans, thiazoles, thiazolidines, pyridines, pyrazines and the like; other sulfur-containing materials including thiols, sulfides, disulfides and the like; proteins; lipids; carbohydrates; so-called flavor potentiators; natural flavoring materials such as cocoa, vanilla, and caramel; essential oils and extracts such as anise oil, clove oil, menthol, carvone and the like; artificial flavoring materials such as vanillin; Virginia tobacco-like taste nuances; and the like; and (b) aromatic materials such as fragrant alcohols, fragrant aldehydes, ketones, nitriles, ethers, lactones, hydrocarbons, synthetic essential oils, natural essential oils, including Virginia tobacco-like aroma nuances and the like; other than the above-identified stress reactivity-reducing substances. Obviously, certain of the optionally includable substances serve as both a flavoring and an aromatizing material, and it should be understood that the added material must be compatible with and complement the active stress reactivity-reducing substance or substances. The quantity of vapor emitting material or beads is chosen, as taught in the aforesaid Warren et al. patent, to evolve, during the act of oral inhalation through the tube 41, a physiologically effective amount of vapor which becomes entrained in the inhalent.

Figure 3:
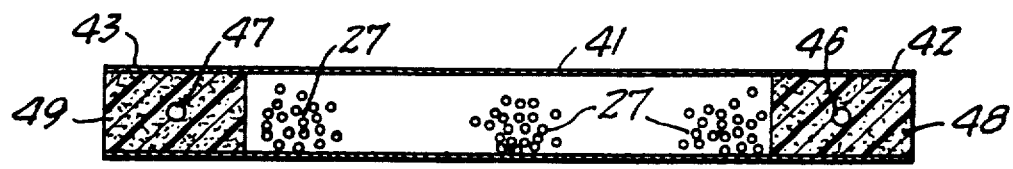
FIG. 3 is a view similar to FIG. 2 showing a modification of the plug ends of the cigarette of FIG. 1.
Figure 4:
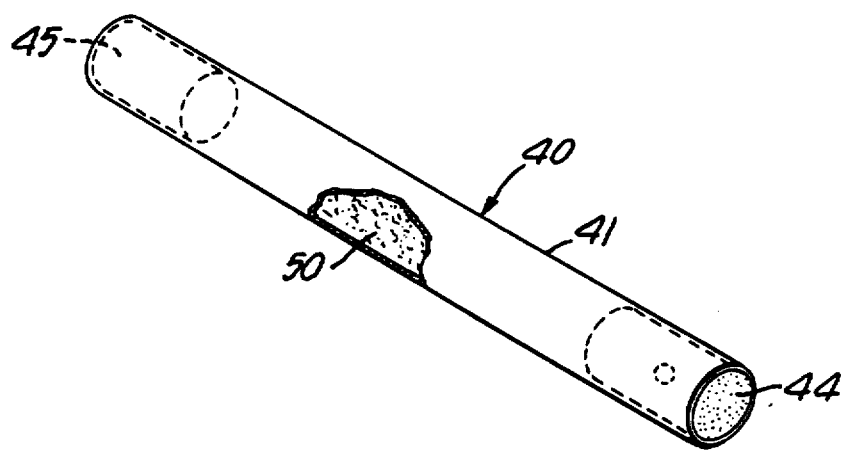
FIG. 4 is a view similar to FIG. 1 but showing another embodiment of the invention.

As shown in FIG. 3, additional beads 46 and 47 can be incorporated in or imbedded in the porous plugs 48 and 49, respectively. It should be understood that instead of including beads in both end plugs, one or more beads can be imbedded in either plug 48 or 49.

The porous plugs 44, 45, 48 and 49 may be produced from any known hydrophobic filter material and by any known method so as to provide end closures for the tube while allowing inhalation through the tube 41 with the drag approximating that of a regular cigarette.

Figure 5:
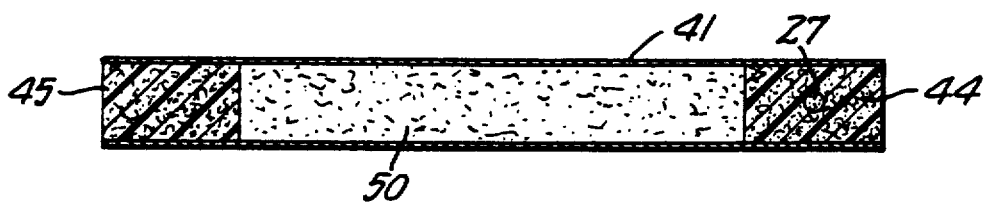
FIG. 5 is a longitudinal sectional view through the cigarette of FIG. 4.
Figure 6:
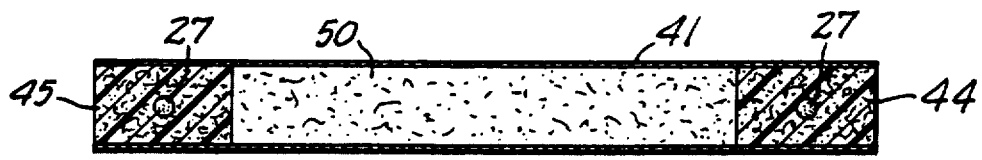
FIGS. 6 and 7 illustrate a view similar to FIG. 5 but illustrating yet another modification thereof.
Figure 7:
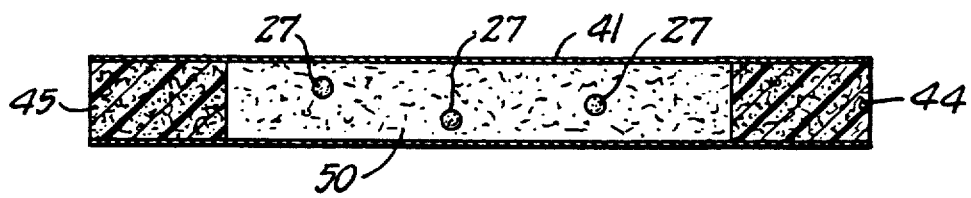

Instead of confining the vapor beads 27 between the end plugs 44 and 45, or 48 and 49, the space within the tube 41 between the porous plugs can be occupied by a porous (vapor permeable) hydrophobic filler material 50 as shown in FIGS. 4 to 7. The material 50 is selected in any known manner to modify the drag imposed upon oral inhalation through tube 41. One or more of the vapor emitting beads 27 can be imbedded within one end plug 44 as shown in FIG. 5, or in both end plugs 44 and 45 as shown in FIG. 6, or in the filler material 50 as shown in FIG. 7, or in various combinations of end plugs and filler material, not shown.

While the embodiment as shown in FIG. 7 suggests a predominance of the filler material, the reverse can be employed with the artifical cigarette 40 being more like that shown in FIG. 2 but with the addition of filler material between plugs 44 and 45 to modify the drag imposed upon oral inhalation through tube 41.

It should be understood that the tube 41 can be constructed in any known manner to resemble a tobacco filled cigarette. One end plug can be surrounded by a filter wrapper or that which resembles a filter wrapper. The remaining body of tube 41 can be formed from a cigarette wrapper or that which resembles such wrapper. The flavoring and/or aromatizing substances can be incorporated by impregnation in the porous plug material and/or the filler material rather than being included in the vapor emitting beads.

Having described the presently preferred embodiments of the subject invention, it should be apparent to those skilled in the subject art that various changes in construction can be introduced without departing from the true spirit of the invention as defined in the appended claims.

What is claimed is:

1. A non-combustible artificial cigarette comprising a tube resembling a cigarette closed at both ends by porous plugs and confining a quantity of a vapor emitting tobacco-free material where said material includes at least one or more stress reactivity-reducing substances selected from the group consisting of nutmeg oil, mace extract, neroli oil, valerian oil, myristicin, elemicin, and isoelemicin, said quantity being chosen sufficient to evolve during the act of oral inhalation through said tube physiologically effective amount of vapor which becomes entrained in the inhalant.

2. A non-combustible artificial cigarette according to claim 1, wherein said vapor emitting material is incorporated in solid beads from which the vapor can evolve, said beads being disposed within said tube.

3. A non-combustible artificial cigarette according to claim 2, wherein said beads include at least one flavor contributing substance selected from the group consisting of saturated, unsaturated, fatty and amino acids; alcohols, including primary and secondary alcohols; esters, carbonyl compounds, including ketones and aldehydes; lactones; cyclic organic materials including benzene derivatives, alicyclics, hetero-cyclics such as furans, thiazoles, thiazolidines, pyridines, and pyrazines; other sulfur-containing materials including thiols, sulfides, and disulfides; proteins; lipids; carbohydrates; so-called flavor potentiators; natural flavoring materials such as cocoa, vanilla, and caramel; essential oils and extracts such as anise oil, clove oil, menthol, and carvone; artificial flavoring materials such as vanillin, Virginia tobacco-like taste nuances; and the like.

4. A non-combustible artifical cigarette according to claim 2, wherein said beads are confined within said tube between said porous plugs.

5. A non-combustible artificial cigarette according to claim 2, wherein the space within said tube between said porous plugs is occupied by a porous filler material to modify the drag imposed upon oral inhalation through said tube, and one or more of said beads are imbedded in at least one of said porous plugs.

6. A non-combustible artificial cigarette according to claim 5, wherein said beads are imbedded in both of said porous plugs.

7. A non-combustible artificial cigarette according to claim 2, wherein a quantity of said beads are confined within said tube between said porous plugs, and additional beads are imbedded in at least one of said porous plugs.

8. A non-combustible artificial cigarette according to claim 2, wherein a quantity of said beads are confined within said tube between said porous plugs, and additional beads are imbedded in both of said porous plugs.

9. A non-combustible artificial cigarette according to claim 2, wherein said beads include a thermoplastic polymer.

10. A non-combustible artificial cigarette according to claim 3, wherein said beads include a thermoplastic polymer.

11. A non-combustible artificial cigarette according to claim 4, wherein said beads include a thermoplastic polymer.

12. A non-combustible artificial cigarette according to claim 5, wherein said beads include a thermoplastic polymer.

13. A non-combustible artificial cigarette according to claim 6, wherein said beads include a thermoplastic polymer.

14. A non-combustible artificial cigarette according to claim 7, wherein said beads include a thermoplastic polymer.

15. A non-combustible artificial cigarette according to claim 8, wherein said beads include a thermoplastic polymer.

16. A non-combustible artificial cigarette according to claim 2, wherein the space within said tube between said porous plugs is occupied by said beads augmented by a porous filler material to modify the drag imposed upon oral inhalation through said tube.

17. A non-combustible artificial cigarette according to claim 1, wherein the space within said tube between said porous plugs is occupied by a porous filler material to modify the drag imposed upon oral inhalation through said tube, and said vapor emitting material is incorporated in said filler material.

* * * * *